United States Patent [19]

Kikuchi

[11] Patent Number: 5,144,647
[45] Date of Patent: Sep. 1, 1992

[54] RADIATION EXPOSURE FIELD LIMITING APPARATUS

[75] Inventor: Hiroshi Kikuchi, Amagasaki, Japan

[73] Assignee: Mitsubishi Denki Kabushiki Kaisha, Tokyo, Japan

[21] Appl. No.: 683,800

[22] Filed: Apr. 11, 1991

[30] Foreign Application Priority Data

Jul. 9, 1990 [JP] Japan ................... 2-179455

[51] Int. Cl.$^5$ .............................................. G21K 1/04
[52] U.S. Cl. .................................... 378/153; 378/150; 250/505.1
[58] Field of Search .................. 378/150–153; 250/505.1

[56] References Cited

U.S. PATENT DOCUMENTS 4,794,629 12/1988 Pastyr et al. ................... 378/152
4,987,309 1/1991 Klasen et al. ................... 378/152

Primary Examiner—Craig E. Church
Attorney, Agent, or Firm—Oblon, Spivak, McClelland, Maier & Neustadt

[57] ABSTRACT

A radiation exposure field limiting apparatus which prevents leakage of X-rays through a gap between each adjacent ones of leaves of radiation shielding blocks and wherein each leaf of the radiation shielding blocks is simplified in sectional shape and can be produced at a reduced cost. The leaves of the apparatus are in the form of plates and are mounted for individual movement relative to each other with respect to a plane of a center axis of radiations generated from a point radiation source to define an exposure field of radiations having an approximated profile to that of an object to be irradiated by such radiations. A face of each of the radiation shielding members at which the radiation shielding member contacts with an adjacent one of the radiation shielding members makes part of a face of a circular cone having the apex at an imaginary radiation source which is imaginarily disposed at a point spaced by a significant distance from the point radiation source.

7 Claims, 6 Drawing Sheets

RADIATION EXPOSURE FIELD LIMITING APPARATUS

BACKGROUND OF THE INVENTION

1. Field of the Invention

This invention relates to an apparatus for limiting a radiation exposure field in an equipment for the radiation therapy or for the non-destructive inspection using radiations, and more particularly to an apparatus for accurately defining a radiation exposure field while preventing radiation leakage from a gap between radiation shielding members.

2. Description of the Prior Art

Conventionally, a radiation exposure field limiting apparatus is incorporated, for example, in a linear electron accelerator for the medical application in which radiations such as, for example, X-rays are generated.

Figure 9:
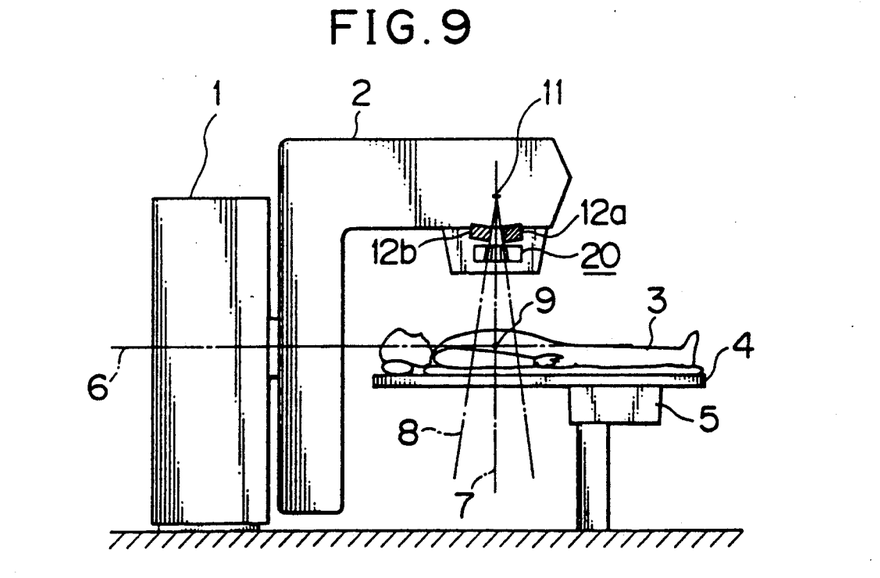
FIG. 9 is a schematic illustration showing an entire linear electron accelerator in which a conventional radiation exposure field limiting apparatus is incorporated.
Figure 10:
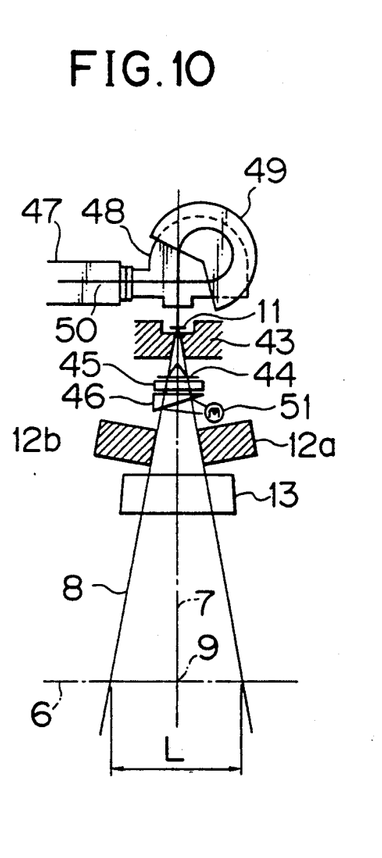
FIGS. 10 and 11 are schematic sectional views as viewed in perpendicular directions from each other illustrating generation of radiations and formation of an exposure field in the linear electron accelerator of FIG. 9.
Figure 11:
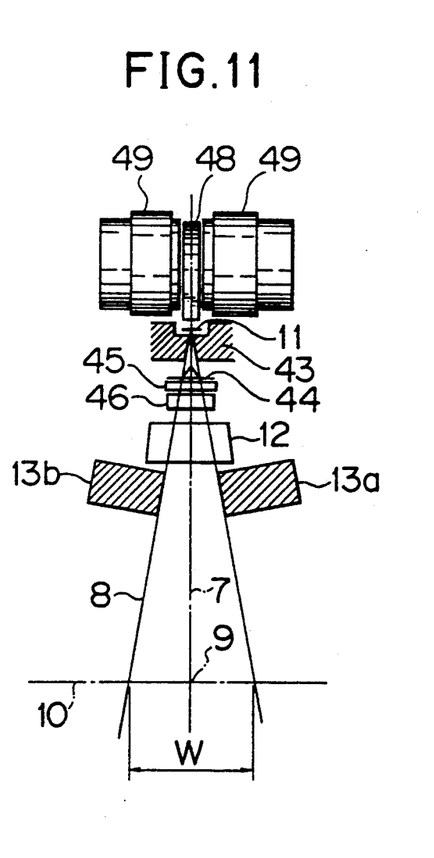

An exemplary one of conventional linear electron accelerators for the medical application is schematically shown in FIG. 9. Referring to FIG. 9, the conventional linear electron accelerator shown includes a fixed frame 1, a rotatable frame 2 supported for rotation around a horizontal axis 6 on the fixed frame 1, and a medical table 5 on which a top plate 4 for supporting thereon a patient to undergo radiation therapy is supported. X-rays 8 are emitted from a radiation source 11 and irradiated along a radiation center axis 7 toward an intersecting point between the axis 6 of rotation of the rotatable frame 2 and the radiation center axis 7 of X-rays 8. Such intersecting point is the center of medical treatment at which the affected part of a patient to be treated is normally positioned and will be hereinafter called an iso-center. Meanwhile, a line 10 shown in FIGS. 11 and 12 which passes the iso-center 9 and extends orthogonally to the axis 6 of rotation and the X-ray radiation center axis 7 will be hereinafter called an exposure field center axis. Referring also to FIGS. 10 and 11, the size of an exposure field to be formed by X-rays 8 generated from the radiation source 11 is defined by a pair of radiation shielding devices 12 and 13 disposed along the X-ray radiation center axis 7 for delineating an exposure field in perpendicular directions to each other and each composed of a pair of radiation shielding members or blocks 12a and 12b or 13a and 13b. The radiation shielding blocks 12a, 12b, 13a and 13b are made of a heavy metal such as lead.

Referring now to FIG. 10, an electron beam 50 emitted from an electron beam source not shown is accelerated by an accelerating tube 47 and then guided by a detecting electromagnet 49 in a beam duct 48 maintained in a vacuum condition so that it is introduced to the radiation source 11 at which X-rays 8 are generated in response to the electron beam 50. A primary collimator 43 for defining a maximum extent of X-rays 8 is disposed just below the radiation source 11, and a flattening filter 44 for making the distribution of X-rays 8 in an exposure field uniform is disposed just below the primary collimator 43. Further, a dose monitor 45 for monitoring an amount of X-rays 8 on the real time basis is disposed just below the flattening filter 44, and a mirror 46 is interposed between the dose monitor 45 and the radiation shielding blocks 12a and 12b. The mirror 46 is disposed such that visible rays of light from a light source 51 may be introduced to provide the same extent as X-rays 8 in order to permit visual observation of an X-ray exposure field. The light source 51 is disposed at a position equivalent to that of the radiation source 11 with respect to the mirror 46.

Referring also to FIG. 11, the dimension of an exposure field which is projected from the radiation source 11 or the light source 51 by way of the radiation shielding blocks 12a and 12b onto a plane including the iso-center 9 and extending orthogonally to the X-ray radiation center axis 7 (such plane will be hereinafter referred to as an iso-center plane) is represented by a capital letter "L", and the dimension of the exposure field which is projected similarly by way of the radiation shielding blocks 13a and 13b onto the iso-center plane is represented by another capital letter "W".

Figure 12:
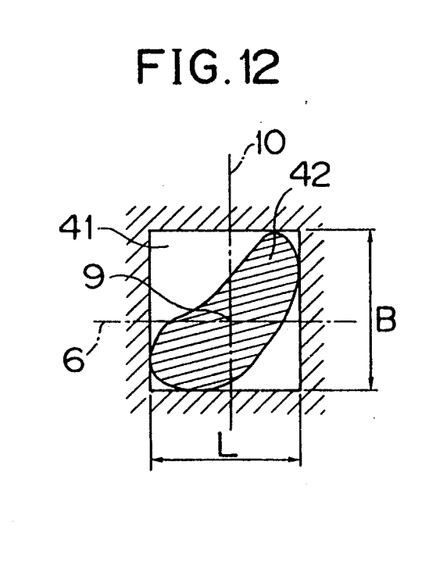
FIG. 12 is a diagrammatic representation showing a relationship between an exposure field formed by the radiation exposure field limiting apparatus shown in FIGS. 10 and 11 and an affected part of a patient.

FIG. 12 shows such exposure field as viewed from the radiation source 11. Referring to FIG. 12, a rectangular area having sides of the dimensions L and W is denoted at 41, and the affected part (such as a tumor) to be medically treated in a body of a patient 3 is denoted at 42.

Figure 13:
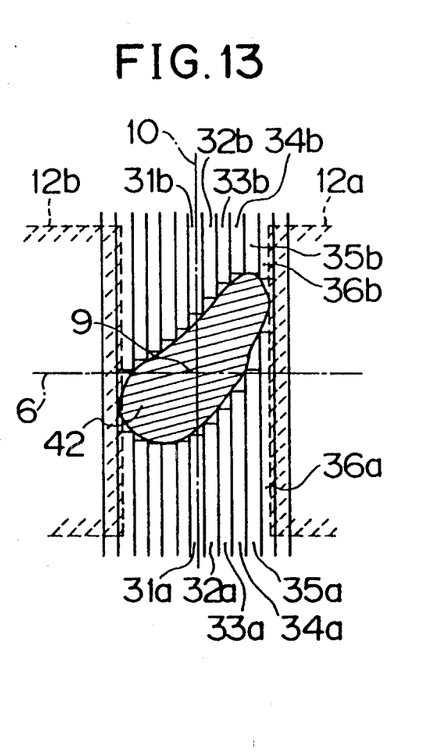
FIG. 13 is a similar view but showing a relationship between an exposure field formed by a radiation exposure field limiting apparatus of the multi-leaf type and an affected part of a patient.

Referring to FIG. 13, each of the radiation shielding blocks 13a and 13b is shown formed from a plurality of radiation shielding members or parts 31a to 36a or 31b to 36b such that they may define an X-ray exposure area of a profile approximated to that of the affected part 42. Such radiation shielding parts 31a to 36a and 31b to 36b will be hereinafter called each a leaf, and here, the leaves 31a and 31b are center leaves which define an exposure area portion W1 along the exposure field center axis 10 while the other leaves are sequentially numbered toward the opposite outer sides from the center leaves 31a and 31b beginning with the number 32. While several leaves on the left-hand side in FIG. 13 of the center leaves 31a and 31b are not denoted by any reference character, they should be considered to be numbered similarly as 32a 36a and 32b to 36b. Accordingly, the radiation shielding blocks 13a and 13b include seven pairs of leaves in the arrangement shown in FIG. 13. Naturally, however, they may include any arbitrary plural number of pairs of leaves. A radiation shielding block including a plurality of leaves will be hereinafter referred to as a multi-leaf radiating shielding block.

Figure 14:
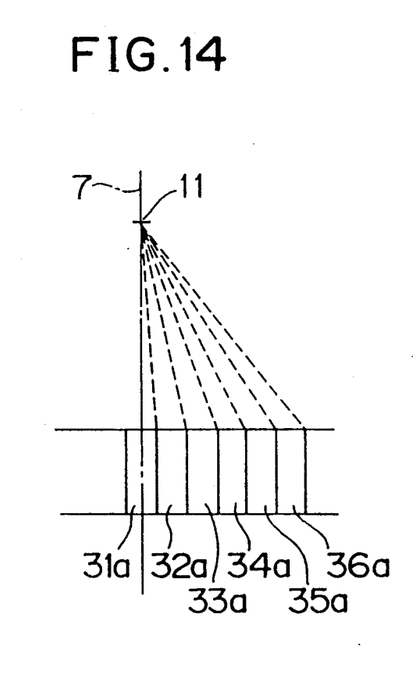
FIG. 14 is a diagrammatic representation showing construction of a conventional radiation exposure field limiting apparatus of the multi-leaf type.

Referring now to FIG. 14, there is shown an exemplary structure of such multi-leaf radiation shielding block as shown in FIG. 13, and each of the radiation shielding blocks 12a and 12b shown in FIG. 10 may be replaced by such multi-leaf radiation shielding block as shown in FIG. 14. Though not shown, the other radiation shielding block 12b or 13b includes leaves 31b to 36b corresponding to the leaves 31a to 36a. In the case of the multi-leaf radiation shielding block shown in FIG. 14, each of the leaves has a rectangular cross section.

Figure 15:
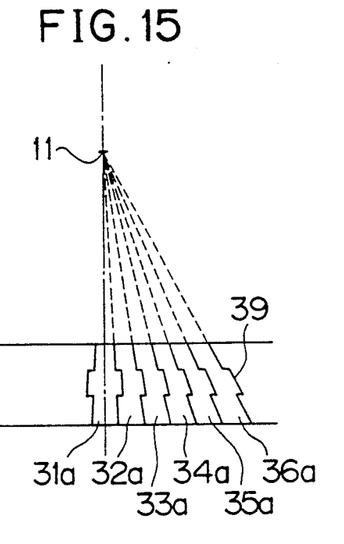
FIG. 15 is a similar view but showing construction of another conventional radiation exposure field limiting apparatus of the multi-leaf type.

FIG. 15 shows another exemplary structure of a multi-leaf radiation shielding block. The multi-leaf radiation shielding block shown in FIG. 15 includes a similar number of leaves which are numbered in a similar manner but have different sectional areas from those of the leaves shown in FIG. 14. In particular, each of the leaves has a sectional area of a generally trapezoidal shape as is provided by cutting a circular cone having the apex at the radiation source 11 along a generating line. In order to prevent X-rays from passing through a gap between each adjacent ones of the leaves, each of the leaves has a projection 39 formed thereon, and the projection 39 is fitted for sliding movement in a complementary recess formed in an opposing face of an outer adjacent one of the leaves.

Figure 16:
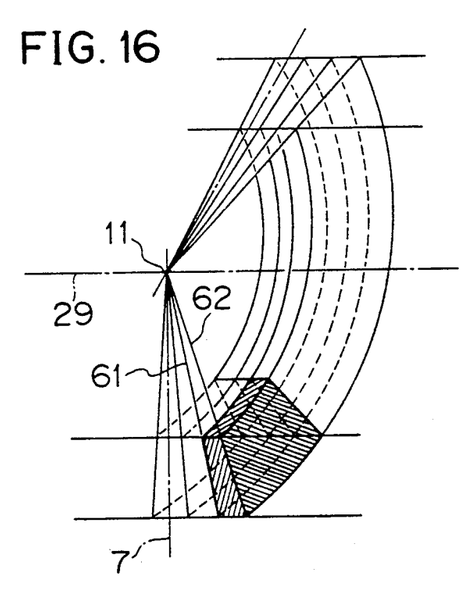
FIG. 16 is a schematic view illustrating a principle of the construction shown in FIG. 15.

FIG. 16 illustrates a principle of construction of each leaf. Referring to FIG. 16, reference numerals 61 and 62 denote generating lines on faces of two circular cones having the apexes commonly at the radiation source 11. Thus, the leaves shown in FIG. 15 are constituted if such a member as is indicated by a hatched portion between the generating lines 61 and 62 in FIG. 16 and similar members as are defined similarly by generating lines are replaced into the individual leaves shown in FIG. 15 and then a projection 39 is provided on each of the leaves while each of the leaves is machined to form a complementary recess in which the projection 39 of an inner adjacent one of the leaves is fitted.

Figure 17:
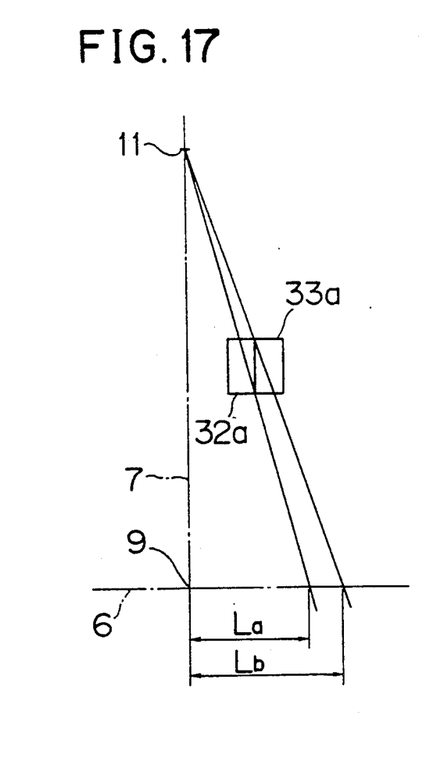
FIGS. 17 and 18 are schematic views illustrating a difference in dimension at portions of an exposure field formed by adjacent leaves arising from a difference between relative positions of the adjacent leaves of the radiation exposure field limiting apparatus shown in FIGS. 14 and 15, respectively.
Figure 18:
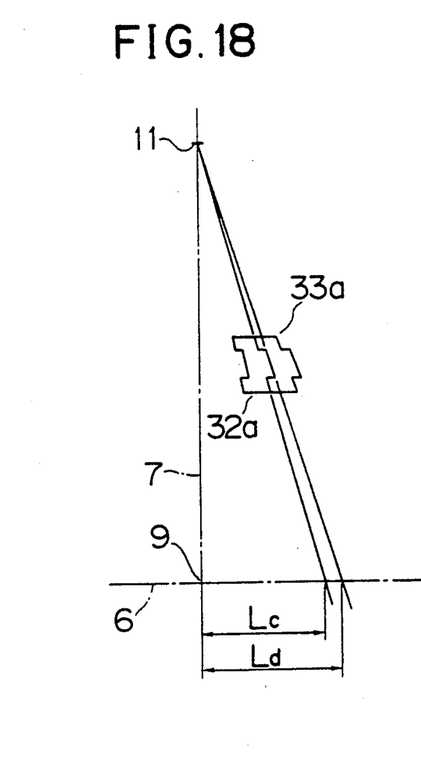

FIGS. 17 and 18 show portions of an exposure field in the direction along L which are formed by such leaves. In particular, FIG. 17 shows, as an example, exposure field portions formed by the leaves 32a and 33a of the radiating shielding block shown in FIG. 14. The exposure field portion projected from the light source 51 is such as denoted by La where the leaf 32a is positioned farther from the axis 6 of rotation than the leaf 33a, but is such as denoted by Lb where the leaf 32a is positioned nearer to the axis 6 of rotation than the leaf 33a. Meanwhile, FIG. 18 shows exposure field portions formed by the leaves 32a and 33a of the radiating shielding block shown in FIG. 15. Similarly, where the leaf 32a is farther from the axis 6 of rotation than the leaf 33a, such an exposure field portion as denoted by Lc is formed, but where the leaf 32a is nearer than the leaf 33a, such another exposure field portion as denoted by Ld is formed.

Subsequently, operation of the linear electron accelerator will be described.

Referring back to FIG. 9, a patient 3 to undergo radiation therapy will first lie on the top plate 4. In order to permit X-rays 8 for the radiation therapy generated from the radiation source 11 to be irradiated from any position around the patient 3, the radiation source 11 can be circularly moved over an angular range greater than 360 degrees around the axis 6 of rotation by means of the rotatable frame 2. Further, the patient 3 can be moved in leftward and rightward directions and in forward and backward directions by means of the top plate 4. Since the top plate 4 can be moved also in upward and downward directions by means of the medical table 5, the affected part 42 of the patient 3 to be irradiated can be positioned in an area including the iso-center 9 to perform radiation therapy.

Referring now to FIGS. 10 and 11 which illustrate a manner of generating X-rays and determining an exposure field, an electron beam 50 is accelerated to a high energy, for example, to 3 to 20 MeV by the accelerating tube 47 and then runs in the beam duct 48 in a vacuum condition while it is deflected by the deflecting electromagnet 49 so that it may be directed toward the patient 3. Consequently, the electron beam 50 is introduced to the radiation source 11 which is made of a metal material which generates X-rays when it is irradiated by an electron beam. The radiation source 11 thus generates intense X-rays 8 in the advancing direction of the electron beam 50. While the X-rays 8 have a forward directivity, the primary collimator 43 is disposed in order to absorb unnecessary X-rays outside a required exposure field. Since the X-rays 8 are spread radially from the radiation source 11 which serves as a point radiation source, the primary collimator 43 is scooped out to form a hole having the profile of a truncated cone having the apex at the radiation source 11, and the X-rays 8 can pass only through the area of the hole. Generally, an exposure field defined by such truncated conical hole of the primary collimator 43 has a maximum dimension specified with the arrangement. Further, since X-rays generally have a directivity, the flattening filter 44 is disposed to make the distribution in intensity of the X-rays 48 uniform, and while such X-rays 48 continue to be generated, the intensity of the X-rays 48 is monitored on the real time basis by means of the dose monitor 45. The X-rays 8 are then stopped by the radiation shielding blocks 12a, 12b and 13a, 13b so that they may be irradiated upon the affected part 42 of the patient 3 in such an exposure field area 41 as seen in FIG. 12. In order to allow visual observation of such exposure field, the mirror 46 is disposed such that visible light which is emitted from the light source 41 disposed at the equivalent position to that of the radiation source 11 with respect to the mirror 46 is reflected by the mirror 46 so that an exposure field of the light may be produced on a face of the skin of the patient 3. Thus, the size of the exposure field, that is, the dimensions L and W can be confirmed from the exposure field of the visible light.

While the linear electron accelerator having a rectangular exposure field operates in such a manner as described above, since X-rays are irradiated also upon normal structure of the patient other than the affected part as seen in FIG. 12, there is the possibility of radiation hazard to such normal structure. Accordingly, a linear electron accelerator in recent years is constituted such that an exposure field is defined by radiation shielding blocks of such multi-leaf construction as shown FIG. 13 so as to assure protection of normal structure. Thus, the radiation shielding blocks 13a and 13b are replaced by those which are formed from leaves 31a to 36a and 31b to 36b, respectively, so that an exposure field in the W direction in FIG. 12 may have several dimensions W1, W2, ... while the exposure field in the L direction is defined by the radiation shielding blocks 12a and 12b. Where such multi-leaf construction is employed, radiation therapy can be achieved with a higher degree of accuracy.

Such multi-leaf radiation shielding blocks as shown in FIG. 14 or 15 have been proposed and produced with an intention to obtain such an exposure field as shown in FIG. 13. In particular, in place of the radiation shielding blocks 13a and 13b, multi-leaf radiation shielding blocks are disposed at the locations of the radiation shielding blocks 13a and 13b which are normally positioned at substantially mid locations between the radiation source 11 and the iso-center 9. In the case of the arrangement shown in FIG. 14 in which a multi-leaf radiation shielding block is viewed from a similar point of view to that in FIG. 10, each leaf has a rectangular cross section. A radiation shielding block is constituted in most cases from an odd plural number of leaves because it is normally necessary to determine the dimension W1 of an exposure field portion along the exposure field center axis and consequently the radiation shielding block includes a center leaf and a pair or pairs of leaves on the opposite sides of the center leaf. In the case of the arrangement of FIG. 14, since the radiation source 11 is not included in a plane of opposing faces of each adjacent ones of the leaves, no X-rays from the radiation source 11 pass through the gaps between the leaves, and accordingly, there is no possibility of direct leakage of X-rays to any locations outside an exposure field. Besides, since each leaf has a profile of a rectangular parallelepiped, it can be worked readily at a low cost. On the other hand, the exposure field defined by such multi-leaf radiation shielding blocks presents such dimensional relationship in the L direction as seen in FIG. 17. In case the dimension of the exposure field in the W direction is greater at the leaf 32a than at the leaf 33a, the dimension of the exposure field in the L direction is such as indicated by La, but on the contrary in case the dimension of the exposure field in the W direction is smaller at the leaf 32a than at the leaf 33a, the dimension of the exposure field in the L direction is such as indicated by Lb, and those dimensions look different from each other. Since X-rays pass more or less obliquely through edge portions of the leaves 32a and 33a, the X-ray exposure field will be dim at portions of the dimensions La and Lb thereof. While the difference between the dimensions La and Lb is small near the center of the exposure field, it may be increased to 1 cm or so at a location of outer leaves.

On the other hand, in the case of the arrangement of FIG. 15, opposing faces of each adjacent ones of the leaves extend along an outer face of a circular cone having the apex at the radiation source 11. Such manner is illustrated in FIG. 16. Referring to FIG. 16, each of leaves has a section in an area between a generating line 61 of a face of a circular cone having the apex at the radiation source 11 and another generating line 62 of a face of another similar circular cone and makes part of a zone defined by and between the two generating lines. The leaves are defined by successive ones of faces of such similar circular cones so that they may be driven to slide along each other without mutually interfering with each other. In this instance, since opposing faces of each adjacent ones of the leaves pass the radiation source 11, if there is only a small gap between adjacent ones of the leaves, X-rays will pass through the gap and reach the patient 3 without being attenuated at all. Accordingly, X-rays may directly leak to a location outside an exposure field, which will make trouble to radiation therapy. Therefore, in the arrangement which employs such multi-leaf shielding blocks as described above, each of the leaves has a pawl 39 formed thereon so as to have such a section as shown in FIG. 15 in order to reduce or prevent such possible leakage of X-rays through gaps between adjacent ones of the leaves. In this instance, the dimension of an exposure field portion or a visually observable exposure field portion in the L direction is such as indicated by Lc in FIG. 18 when the dimension of the exposure field in the W direction is greater at the leaf 32a than at the leaf 33a, but on the contrary when the dimension of the exposure field in the W direction is smaller at the leaf 32a than at the leaf 33a, the dimension of the exposure field portion in the L direction is such as indicated by Ld in FIG. 18. Normally, the difference between the dimensions Lc and Ld is 3 to 4 mm, and since the thickness of each leaf is smaller at a portion thereof adjacent a leaf gap than at any other portion thereof, the X-ray shielding effect at such portion is lower than any other portion. Besides, the production cost of such leaves is high.

In this manner, radiation therapy is conventionally performed with a linear electron accelerator for the medical application in which such a radiation exposure field limiting apparatus of the multi-leaf type as described above is incorporated.

Since a conventional radiation exposure field limiting apparatus of the multi-leaf type is constructed in such a manner as described above, where such structure as shown in FIG. 14 is employed, the difference between the dimensions La and Lb is significantly great at an end portion of an exposure field, and a medical treatment project must necessarily be put into operation taking such difference into consideration. On the other hand, where such structure as shown in FIG. 15 is employed, since such difference between Lc and Ld exists for each leaf although it is small, it is similarly difficult to make a medical treatment project, and besides inadvertent undesirable linear leakage of X-rays to a location outside an exposure field cannot be avoided. In addition, since the profile of each leaf is complicated, the production cost is high.

SUMMARY OF THE INVENTION

It is an object of the present invention to provide a radiation exposure field limiting apparatus which prevents leakage of X-rays through a gap between each adjacent ones of leaves of radiation shielding blocks.

It is another object of the present invention to provide a radiation exposure field limiting apparatus which minimizes a difference between dimensions of portions of a visually observable exposure field formed by adjacent ones of leaves of radiation shielding blocks arising from a difference between relative positions of the adjacent leaves.

It is a further object of the present invention to provide a radiation exposure field limiting apparatus wherein each leaf of radiation shielding blocks is simplified in sectional shape and can be produced at a reduced cost.

In order to attain the objects, according to the present invention, there is provided a radiation exposure field limiting apparatus for limiting an exposure field to be formed by radiations generated from a radiation generating equipment which includes a particle accelerator and a point radiation source, which comprises a plurality of radiation shielding members in the form of plates for defining an exposure field of radiations, the radiation shielding members being mounted for individual movement relative to each other with respect to a plane of a center axis of radiations generated from the point radiation source to define an exposure field of radiations having an approximated profile to that of an object to be irradiated by such radiations, a face of each of the radiation shielding members at which the radiation shielding member contacts with an adjacent one of the radiation shielding members making part of a face of a circular cone having the apex at an imaginary radiation source which is imaginarily disposed at a point spaced by a significant distance from the point radiation source.

With the radiation exposure field limiting apparatus, since the apex of the face of the circular cone part of which is made by a face of each radiation shielding member is disposed at a position different from the position of the point radiation source, radiations which may otherwise pass through gaps between the radiation shielding members are eliminated, and an intended radiation exposure field can be formed clearly. Further, the difference between visually observable exposure field portions which may arise from a difference between relative positions of adjacent radiation shielding members can be restricted within an allowable range, and since the radiation shielding members are simplified in construction, they can be produced readily. Consequently, radiations can be irradiated with a high degree of accuracy and an equipment in which the radiation exposure field limiting apparatus is incorporated can be produced at a reduced cost.

The above and other objects, features and advantages of the present invention will become apparent from the following description and the appended claims, taken in conjuction with the accompanying drawings.

DESCRIPTION OF THE PREFERRED EMBODIMENTS

Figure 1:
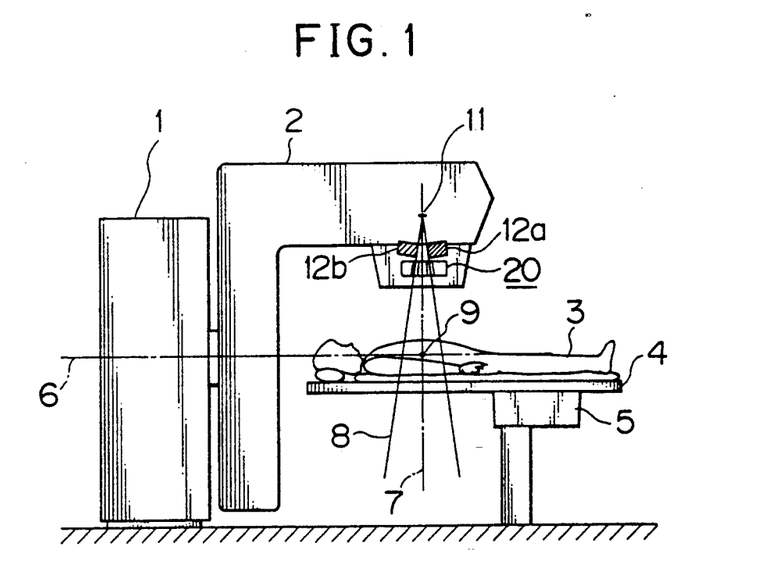
FIG. 1 is a schematic illustration showing an entire linear electron accelerator in which a radiation exposure field limiting apparatus according to the present invention is incorporated.

Referring first to FIG. 1, there is shown a linear electron accelerator in which a radiation exposure field limiting apparatus according to the present invention is incorporated. The linear electron accelerator shown is substantially similar in construction to the conventional electron accelerator shown in FIG. 9, and description of common construction is omitted herein to avoid redundancy. The linear electron accelerator of FIG. 1 is different from the conventional linear accelerator in that it includes a pair of radiation shielding blocks 20 of the multi-leaf type in place of the radiation shielding blocks 13a and 13b.

Figure 2:
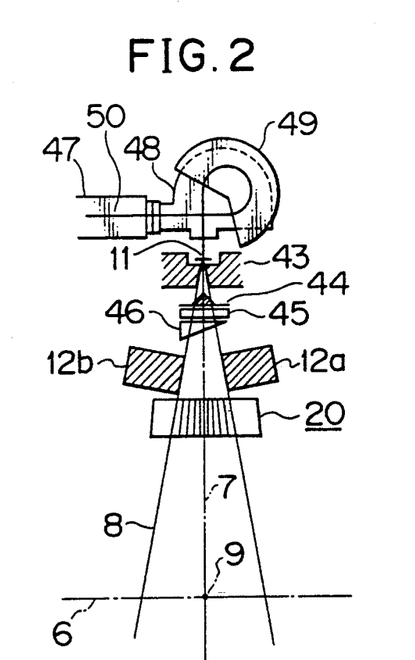
FIG. 2 is a schematic sectional view illustrating generation of radiations and formation of an exposure field in the linear electron accelerator of FIG. 1.
Figure 3:
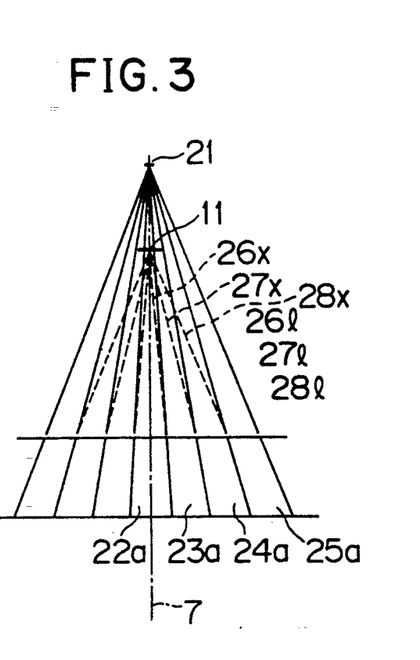
FIG. 3 is a diagrammatic representation showing a multi-leaf radiation exposure field limiting apparatus to which the present invention is applied.

FIG. 2 is a similar view to FIG. 10 but shows an apparatus for generating X-rays and a radiation exposure field limiting apparatus for defining an exposure field to which the present invention is applied, and FIG. 3 is a similar view to FIG. 14 but shows one of the radiation shielding blocks 20 shown in FIGS. 1 and 2. Referring to FIGS. 2 and 3, each of the radiation shielding blocks 20 is composed of a plurality of radiation shielding members or leaves including a center leaf 22a for defining an exposure field portion on a center axis of an exposure field to be formed and a suitable plural number of, three in the arrangement shown in FIG. 3, pairs of leaves 23a, 24a and 25a disposed in a symmetrical relationship on the opposite sides of the center leaf 22a. Though not shown, corresponding leaves of the other radiation shielding block 20 are disposed in an opposing relationship to the leaves 22a to 25a of the one radiation shielding block 20 in such a manner as in the radiation shielding blocks shown in FIG. 13. The leaves 22a to 25a of the radiation shielding blocks 20 are connected to be driven independently of each other by respective suitable driving mechanism not shown so that portions W1, W2, . . . of the exposure field may be defined independently of each other. The leaves 22a to 25a, however, may be driven to move such that they may be moved subordinately by adjacent ones or opposing ones thereof.

The leaves 22a to 25a of the radiation shielding blocks 20 are constructed so as to have a common imaginary radiation source at a location denoted at 21 on a radiation center axis 7. In particular, each of the leaves 22a to 25a has an outer face at which it contacts with an inner face of an outer adjacent leaf and which makes part of a face of a circular cone having the apex at the imaginary radiation source 21, and a generating line of such face of the circular cone is denoted by 26l, 27l or 28l. Thus, for example, reference character 26l denotes a generating line of a face of a circular cone which is provided by an outer face of the leaf 22a contacting with an inner face of the outer adjacent leaf 23a and has the apex at the imaginary radiation source 21. Meanwhile, reference characters 25x, 26x and 27x denote X-rays which come to the outer faces of the leaves 22a, 23a and 24a from an actual radiation source 11.

Figure 4:
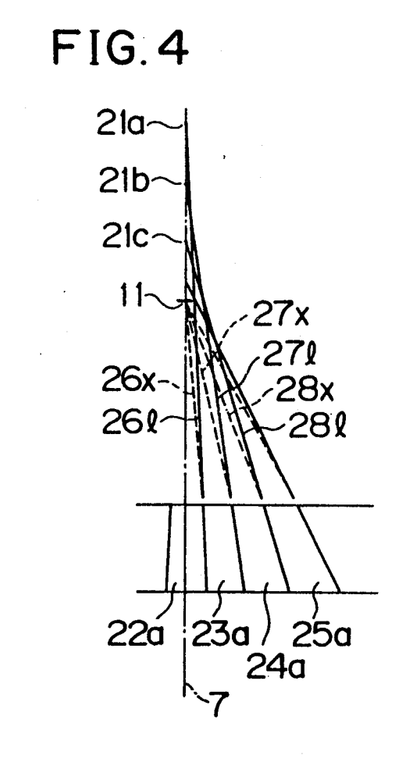
FIG. 4 is a similar view but showing a modified multi-leaf radiation exposure field limiting apparatus.

Referring now to FIG. 4, there is shown a modification to the radiation shielding block shown in FIG. 3. The radiation shielding block shown is modified such that the individual leaves 22a to 25a do not have a common imaginary radiation source but have different imaginary radiation sources on the center axis 7. In particular, a generating line 26l of a face of a circular cone of an outer face of the center leaf 22a has an imaginary radiation source at the apex 21a of the circular cone, and generating lines 27l and 28l of faces of circular cones of outer faces of the leaves 23a and 24a have imaginary radiation sources at the apexes 21b and 21c, respectively.

Figure 5:
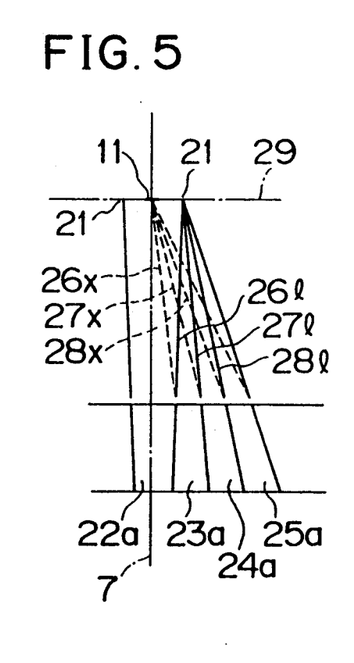
FIG. 5 is a similar view but showing another modified multi-leaf radiation exposure field limiting apparatus.

Referring now to FIG. 5, there is shown another modification to the radiation shielding block shown in FIG. 3. The radiation shielding block shown is modified such that the individual leaves 22a to 25a have a common imaginary radiation source 21 on an axis 29 which passes the actual radiation source 11 and extends in parallel to the axis 6 of rotation of the rotatable frame 2. Such axis 29 will be hereinafter referred to as an imaginary radiation source axis.

Figure 6:
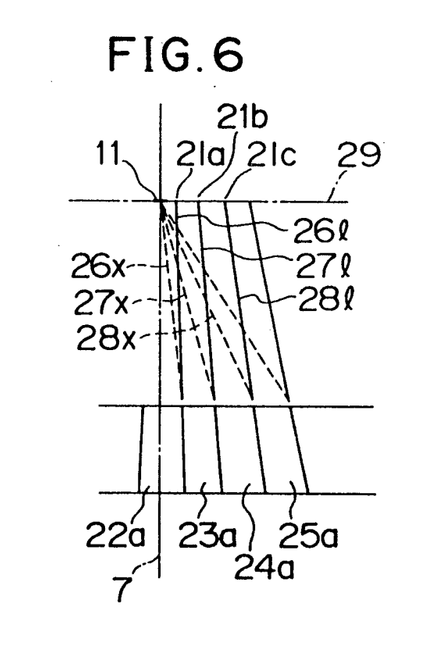
FIG. 6 is a similar view but showing a modification to the modified multi-leaf radiation exposure field limiting apparatus of FIG. 5.

Referring now to FIG. 6, there is shown a modification to the modified radiation shielding block shown in FIG. 5. The radiation shielding block shown is modified such that the leaves 22a to 24a have different imaginary radiation sources 21a to 21c on the imaginary radiation source axis 29, that is, the generating lines 26l to 28l of faces of circular cones of outer faces of the leaves 22a to 24a intersect the imaginary radiation source axis 29 at different positions.

Figure 7:
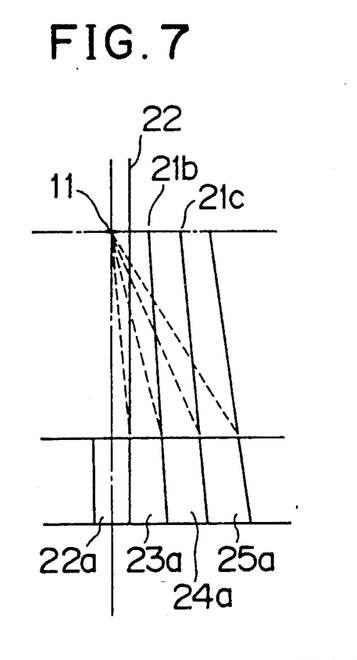
FIG. 7 is a similar view but showing a further modification to the multi-leaf radiation exposure field limiting apparatus shown in FIG. 3.

Referring now to FIG. 7, there is shown a modification to the radiation shielding block shown in FIG. 6. The radiation shielding block shown is modified such that an outer face of the center leaf 22a which contacts with an inner face of the outer adjacent leaf 23a does not make part of a face of a circular cone but makes a plane which includes a line 22l parallel to the radiation center axis 7 and extends perpendicularly to the imaginary radiation source axis 29, that is, a flat plane. Consequently, the center leaf 22a has a rectangular cross section as seen in FIG. 7. The other leaves 23a and 24a have outer faces which make part of faces of circular cones having the apexes at imaginary radiation sources 21b and 21c, respectively, on the imaginary radiation source axis 29.

Figure 8:
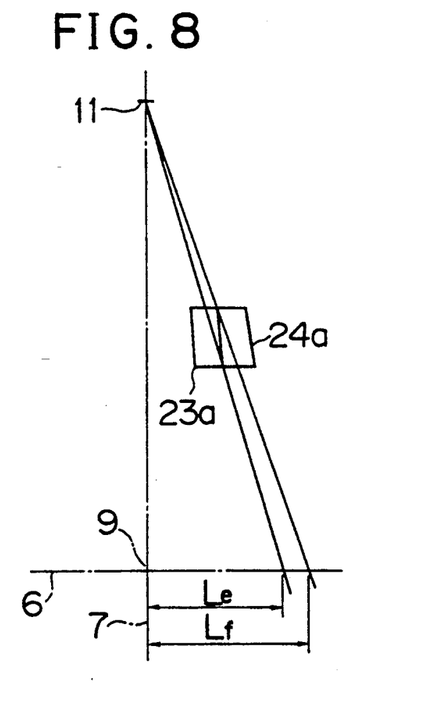
FIG. 8 is a schematic view illustrating a difference in dimension at portions of an exposure field formed by adjacent leaves arising from a difference between relative positions of the adjacent leaves.

FIG. 8 is a view similar to FIGS. 17 and 18 but shows a manner in which a difference in visually observable exposure field portions is provided by a difference in mutual positions of adjacent leaves of any of such radiation shielding blocks shown in FIGS. 3 to 7.

Subsequently, operation of the linear electron accelerator will be described.

Referring back to FIG. 1, X-rays 8 are generated from the radiation source 11 and restricted in exposure field thereof by the radiation shielding blocks 12a and 12b and then by the radiation shielding blocks 20 so that it is used for the radiation therapy of a patient 3. FIG. 2 illustrates a manner of generation of X-rays and definition of an exposure field similarly as FIG. 10, but the radiation shielding blocks 13a and 13b of FIG. 10 are replaced here by the multi-leaf radiation shielding blocks 20. The leaves of the multi-leaf radiation shielding blocks 20 operate in one of such manners as seen in FIGS. 3 to 7 wherein faces of circular cones defined by them do not have the apex at the radiation source 11 but have the apex or apexes at the imaginary radiation source 21 or sources 21a to 21c.

In particular, referring to FIG. 3, faces of the leaves 22a to 25a which contact with each other make part of faces of circular cones, and they have a common apex at the imaginary radiation source 21 spaced from the actual radiation source 11. If the actual radiation source 11 is located at the position of the imaginary radiation source, then X-rays from the same directly pass through gaps between adjacent ones of the leaves and make leakage X-rays outside the intended exposure field, which will make trouble to intended radiation therapy. Actually, however, since the actual radiation source 11 is located at a different position from the imaginary radiation source 21 in the present arrangement, leakage X-rays outside the intended exposure field are prevented by the radiation shielding blocks 20. In particular, taking an X-ray 26x as an example, the X-ray 26x which comes to a gap (represented by a generating line 26l) between the leaves 22a and 23a cannot pass through the gap linearly.

Now, if it is assumed tha the leaf gap is 0.1 mm and a lower end of the leaf 22a remote from the actual radiation source 11 is spaced by 50 cm from the actual radiation source 11 while the leaf 22a has a thickness equal to 70 mm in the direction of the radiation center axis, then X-rays which may pass directly through the leaf gap can be prevented if the imaginary radiation source 21 is located at a position spaced by 60 mm on the radiation center axis from the actual radiation source 11. In actual designing, such dimensions may be set to values having some tolerance, but they will be determined taking a magnitude in displacement between visually observable exposure field portions arising from relative positions of adjacent leaves into consideration. In the case of the dimensions given above, the difference in visually observable exposure field portions with respect to the leaf 22a, that is, the difference between the dimensions Le and Lf shown in FIG. 8, is 0.2 mm or so on the iso-center plane. The dimension of the leaf gap specified above is a value which is almost applicable to a linear electron accelerator wherein the distance between the radiation source 11 and the iso-center 9 is 1 m in most cases and which is operating actually in the technical field. Further, from an ordinary case in the field of medical treatment wherein an error of 1 mm in visual observation of an X-ray exposure field by visible light is permitted, the error of 0.2 mm in visual observation is a sufficiently small value. Accordingly, the imaginary radiation source 21 can be spaced by a greater distance from the actual radiation source 11. Since such error in visual observation is greater at an outer side leaf, the position of the imaginary radiation source should be determined with a maximum value of such errors in visual observation.

An investigation must also be made for leakage X-rays which may pass in a scattered condition through any leaf gap in the system in which no X-rays pass directly through such leaf gap. A concept of leakage which is normally called streaming can be applied to such leakage. Such leakage does not amount to a significant value because the leaf gap is 0.1 mm or so (a further smaller value can be achieved actually) and very small but amounts to such a value which is resulted from attenuation of X-rays while they pass through a leaf as a radiation shielding material. An ordinary system is designed such that X-rays may be attenuated normally to one hundredth or less when they pass through a leaf (of each of the radiation shielding blocks 12a, 12b, 13a and 13b).

Where the multi-leaf radiation shielding blocks are designed in such a manner as described above, the difference between visually observable exposure field portions arising from a difference between relative positions of adjacent leaves which has been called in question hereinabove with reference to FIG. 14 can be restricted to a value sufficiently lower than an allowable value, and direct passage of X-rays through a leaf gap which has been called in question hereinabove with reference to FIG. 15 can be achieved without employing such projection 39 as seen in FIG. 15. Accordingly, the multi-leaf radiation shielding blocks are simple in structure, easy to produce and economical, and restrict leakage of X-rays outside an exposure field to an allowable level as different from insufficient attenuation of directly passing X-rays by the projections 39. Besides, shading off or a penumbla around an edge portion of an exposure field of X-rays which is a common problem to the arrangements shown in FIGS. 14 and 15 is minimized or moderated significantly because the faces of the leaves extend along radiation planes of X-rays, which enables medical treatment with a low penumbla Accordingly, there are significant effects in the field of medical treatment that medical treatment planning is facilitated and that accuracy in medical treatment is improved.

Since in the arrangement shown in FIG. 3 the difference between the dimensions Le and Lf shown in FIG. 8 increases toward the opposite outer sides from the center leaf 22a as described above, the arrangement shown in FIG. 4 is constituted otherwise such that the generating lines 26l, 27l and 28l for the leaves 22a, 23a and 24a pass the different imaginary radiation sources 21a, 21b and 21c, respectively, so that the difference between adjacent visually observed exposure field portions shown in FIG. 18 (difference between Le and Lf) may be restricted to a sufficiently small value within an allowance and such differences may be substantially similar values for the individual leaves in order to assure medical treatment with X-rays having penumblas which are equal at any position of the affected portion 42. It is to be noted that different leaves may have a common imaginary radiation source depending upon the difference between the dimensions Le and Lf.

On the other hand, the arrangement shown in FIG. 5 is constructed such that the common imaginary radiation source 21 is positioned on the imaginary radiation source axis 29. The radiation shielding blocks 13a and 13b shown in FIG. 11 make opening and closing movement so as to normally make generating lines of a circular cone having the apex at the actual radiation source 11 in order to define an exposure field. In the case of the arrangements shown in FIGS. 3 and 4, the apexes of similar generating lines assume different positions from the radiation source 11 in the condition shown in FIG. 11, and consequently, an exposure field will have some penumblas at the opposite boundaries in the W direction. Thus, if the generating lines have the imaginary radiation source 21 on the imaginary radiation source axis 29 as shown in FIG. 5, then the imaginary radiation source 21 and the actual radiation source 11 are overlapped with each other in FIG. 11. Consequently, there is an effect that penumblas of an exposure field in the W direction can be prevented.

The arrangement shown in FIG. 6 is somewhat similar in construction to the arrangement shown in FIG. 6 but is modified such that the imaginary radiation sources 21a, 21b and 21c are disposed at different positions on the imaginary radiation source axis 29 in order to attain an effect that differences between the distances Le and Lf of all of the leaves are made substantially equal to each other similarly as in the modification of the arrangement of FIG. 4 to the arrangement of FIG. 3. Also in this instance, different leaves may have a common imaginary radiation source depending upon a degree of the difference between the dimensions Le and Lf.

The arrangement shown in FIG. 7 is a most practical arrangement and includes the center leaf 22a which has a rectangular cross section. Since the center leaf 22a has the opposite faces which are located at the innermost positions among other faces of the leaves of the radiation shielding block, even where it has such a rectangular cross section, the difference between the dimensions Le and Lf shown in FIG. 18 is sufficiently small. In this instance, if the leaf faces are formed not as faces of circular cones (curved faces) but as flat faces in order to facilitate working of the leaves, then a significant effect is provided that production of the leaves is easy. Further, if the difference between the dimensions Le and Lf of a visually observable irradiation field portion is smaller than an allowable value, not only the center leaf 22a but also an adjacent pair or pairs of leaves on the opposite sides of the center leaf 22a may have a rectangular cross section or sections. Such modification as is made in the arrangement shown in FIG. 7 can be applied to any of the radiation shielding blocks shown in FIGS. 3 to 7.

It is to be noted that while in the embodiment described above a radiation exposure field limiting apparatus of the present invention is incorporated in a linear electron accelerator for the X-ray medial treatment, it can be incorporated similarly in any other radiation generating equipment which generates X-rays such as a cobalt 60 equipment, a betatron, a microtron and a synchrotron and also in an X-ray generating equipment which generates X-rays of energy lower than 1 MeV. Further, a radiation exposure field limiting apparatus of the present invention can be applied to any other radiations than X-rays such as an electron beam, gamma-rays, a neutron beam, a proton beam and a corpuscular beam, and a radiation shielding block may be made of a material which is effective for radiations to be used, such as a heavy metal for X-rays, a light metal for an electron beam and paraffin or an acrylic resin material for a neutron beam in order to attain intended similar effects.

Further, similar effects can be attained also where, in distribution of radiations for any other application than for the medical treatment, that is, in non-destructive inspection with radiations, an exposure field is defined by means of multi-leaf radiation shielding members in order to prevent possible fading of an image of a portion for the inspection arising from scattered light.

It is to be noted that, while the multi-leaf radiation shielding blocks 20 shown in FIG. 2 replace the radiation shielding blocks 13a and 13b of the system shown in FIG. 10, they may otherwise replace the radiation shielding blocks 12a and 12b shown in FIG. 10.

Having now fully described the invention, it will be apparent to one of ordinary skill in the art that many changes and modifications can be made thereto without departing from the spirit and scope of the invention as set forth herein.

What is claimed is:

1. A radiation exposure field limiting apparatus for limiting an exposure field to be formed by radiations generated from a radiation generating equipment which includes a particle accelerator and a point radiation source, comprising a plurality of radiation shielding members in the form of plates for defining an exposure field of radiations, said radiation shielding members being mounted for individual movement relative to each other with respect to a plane of a center axis of radiations generated from said point radiation source to define an exposure field of radiations having an approximated profile to that of an object to be irradiated by such radiations, a face of each of said radiation shielding members at which the radiation shielding member contacts with an adjacent one of said radiation shielding members making part of a face of a circular cone having the apex at an imaginary radiation source which is imaginarily disposed at a point spaced by a significant distance from said point radiation source.

2. A radiation exposure field limiting apparatus as claimed in claim 1, wherein the imaginary radiation sources of said radiation shielding members are located at a common point on the center axis of radiations spaced from said point radiation source.

3. A radiation exposure field limiting apparatus as claimed in claim 1, wherein the imaginary radiation sources of said radiation shielding members are located at different points on the center axis of radiations spaced from said point radiation source.

4. A radiation exposure field limiting apparatus as claimed in claim 1, wherein the imaginary radiation sources of said radiation shielding members are located at a common point spaced from said point radiation source on an axis which passes said point radiation source and extends orthogonally to the center axis of radiations and also to the direction of movement of said radiation shielding members.

5. A radiation exposure field limiting apparatus as claimed in claim 1, wherein the imaginary radiation sources of said radiation shielding members are located at different points spaced from said radiation source on an axis which passes said radiation source and extends orthogonally to the center axis of radiations and also to the direction of movement of said radiation shielding members.

6. A radiation exposure field limiting apparatus as claimed in claim 1, wherein said radiation shielding members are disposed in a pair of opposing sets each including an odd plural number of such radiation shielding members, one of said radiation shielding members in each set which is located at the center of said radiation shielding members of the set and defines a portion of an exposure field of radiations which intersects the center axis of radiations having a pair of faces at which the one radiation shielding member contacts with adjacent ones of said radiation shielding members of the set and which make part of flat planes which extend in parallel to the center axis of radiations while each of the other radiation shielding members of the set has a pair of faces which make part of a face of a circular cone having the apex at said imaginary radiation source of the radiation shielding member.

7. A radiation exposure field limiting apparatus as claimed in claim 6, wherein also each of an adjacent pair or pairs of the other radiation shielding members in each set on the opposite sides of the center radiation shielding member has a pair of faces which make part of flat planes which extend in parallel to the center axis of radiations.

* * * * *